United States Patent
Ranganathan et al.

(10) Patent No.: US 10,617,887 B2
(45) Date of Patent: Apr. 14, 2020

(54) METHOD TO REDUCE LOCAL HOT/COLD SPOTS IN DMPO-BASED IMRT PLANNING

(71) Applicant: KONINKLIJKE PHILIPS N.V., Eindhoven (NL)

(72) Inventors: Vaitheeswaran Ranganathan, Bangalore (IN); Gipson Joe Anto, Kaliyal (IN); Prashant Kumar, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 291 days.

(21) Appl. No.: 15/534,697

(22) PCT Filed: Dec. 4, 2015

(86) PCT No.: PCT/IB2015/059375
§ 371 (c)(1),
(2) Date: Jun. 9, 2017

(87) PCT Pub. No.: WO2016/092441
PCT Pub. Date: Jun. 16, 2016

(65) Prior Publication Data
US 2017/0361127 A1   Dec. 21, 2017

(30) Foreign Application Priority Data
Dec. 11, 2014   (IN) ............................ 6251/CHE/2014

(51) Int. Cl.
*A61N 5/00* (2006.01)
*A61N 5/10* (2006.01)

(52) U.S. Cl.
CPC ......... *A61N 5/1031* (2013.01); *A61N 5/1081* (2013.01); *A61N 2005/1074* (2013.01); *A61N 2005/1089* (2013.01)

(58) Field of Classification Search
CPC ........ A61N 5/00; A61N 5/1001; A61N 5/103; A61N 5/1031; A61N 5/1081
USPC ........................................................ 600/1–8
See application file for complete search history.

(56) References Cited

U.S. PATENT DOCUMENTS

| | | |
|---|---|---|
| 7,529,339 B2 | 5/2009 | Goldman et al. |
| 2012/0136677 A1 | 5/2012 | Ziegenhein et al. |
| 2013/0197878 A1 | 8/2013 | Fiege et al. |
| 2016/0089549 A1 | 3/2016 | Ranganathan et al. |

OTHER PUBLICATIONS

Cotrutz, C. et al., "IMRT dose shaping with regionally variable penalty scheme", Med. Phys. 2003; 30 544-51.
Vaitheeswaran, R. et al., "TU-A-BRA-05: An algorithm for Automated Determination of IMRT Objective Function Parameters," Medical Physics, 37(6), 3369-3369, 2010.
Greef, M. de et al., "Accelerated ray tracing for radiotherapy dose calculations on a GPU", Medical Physics 36, 4095 (2009).
Fox, C. et al., "Fast voxel and polygon ray-tracing algorithms in intensity modulated radiation therapy treatment planning", Medical Physics 33, 1364 (2006).

(Continued)

*Primary Examiner* — John P Lacyk

(57) ABSTRACT

A method and related system to adjust an existing treatment plan. A second optimization is run based on a dual objective function system that includes a first objective function used for the optimization in respect of the existing plan and a second, extended objective function that includes the said first objective function as a functional component.

17 Claims, 3 Drawing Sheets

(56) References Cited

OTHER PUBLICATIONS

Xhaferllari, I. et al., "Automated IMRT planning with regional optimization using planning scripts", Journal of Applied Clinical Medical Physics, vol. 14, No. 1 (2013).
Suss, P. et al., "Paper: The critical spot eraser a method to interactively control the correction of local hot and cold spots in IMRT planning". Physics in Medicine and Biology, Institute of Physics Publishing, Bristol GB, vol. 58, No. 6, Feb. 27, 2013, pp. 1855-1867.

METHOD TO REDUCE LOCAL HOT/COLD SPOTS IN DMPO-BASED IMRT PLANNING

CROSS-REFERENCE TO PRIOR APPLICATIONS

This application is the U.S. National Phase application under 35 U.S.C. § 371 of International Application Serial No. PCT/IB2015/059375, filed on Dec. 4, 2015, which claims the benefit of Indian Application Serial No. 6251/CHE/2014, filed on Dec. 11, 2014. These applications are hereby incorporated by reference herein.

The invention relates to a method for adjusting a first specification of a dose distribution in an object to be exposed to radiation by means of a radiation dispenser, to an apparatus for adjusting a first specification of a dose distribution in an object to be exposed to radiation by means of a radiation dispenser, to a computer program product, and to a computer readable medium.

BACKGROUND OF THE INVENTION

Cancer remains one of the scourges of mankind and radiation therapy is one of the chief tools to combat same. In radiation therapy a high energy treatment radiation beam is used to destroy cancerous tissue whilst sparing healthy one.

A particular type of radiation therapy planning called Intensity Modulated Radiotherapy (IMRT) allows spatially modulating a treatment beam to precisely conform not only in shape but also in terms of prescribed dosage requirements as per a treatment plan.

A treatment plan is computed using numerical optimization based on an objective function that defines a number of dose objectives or dose-volume objectives. Although a plan may globally comply with these objectives, there may still remain local deficiencies. For instance, some parts of the cancerous region may receive more than the required dose or may receive less than the required dose.

Although there are systems to "tweak" an existing treatment plan (see for instance C Cotrutz and L Xing, "IMRT dose shaping with regionally variable penalty scheme", Med. Phys. 2003; 30 544-51), these are sometimes not easy to operate. Any modification made to the beam arrangement or the objective function parameters of the current treatment plan in view of removing such local deficiencies could lead to big changes in the dose distribution. In particular, the magnitude and type of change is beyond the direct influence of the user and could lead to several manual backtracking steps.

SUMMARY OF THE INVENTION

There may therefore be a need in the art for an alternative method to adjust a radiation treatment plan.

The object of the present invention is solved by the subject matter of the independent claims where further embodiments are incorporated in the dependent claims.

It should be noted that the following described aspect of the invention equally apply to the apparatus for adjusting a first specification of a dose distribution in an object to be exposed to radiation by means of a radiation dispenser, to the computer program product, and to the computer readable medium.

According to a first aspect of the invention, there is provided a method of adjusting a first specification of a dose distribution in an object to be exposed to radiation by means of a radiation dispenser, said specification computed based on a first objective function, the objective function defining a dose requirement for at least one respective locations in an object in terms of a respective machine setting for said radiation dispenser, the method comprising the steps of:

based on the first specification, identifying at least one location for which a respective dose requirement as per the first objective function is not met relative to a threshold;

receiving a new dose requirement for the identified at least one location;

computing a second specification based on two objective functions including the first objective function and a second, an extend objective function, formed from the first objective function, wherein the extended objective functions includes at least one of the dose requirements as per the first objective function in addition to the new dose requirement.

According to one embodiment, the method comprises classifying the machine settings into two groups, into a critical group and a non-critical group, wherein a machine setting associable with the at least one identified object location is classified into the critical group, whereas a machine setting associable with the or different object location is classified into the non-critical group if the respective dose requirement as per the first objective function is met.

According to one embodiment, there are more machine settings in the non-critical group than there are in the critical group.

According to one embodiment, the first objective function is restricted to the non-critical group of machine settings and wherein the second objective function is restricted to the critical group of machine settings.

According to one embodiment, the second objective function includes at least one user adjustable weight factor to weight a contribution of the first objective function to the second objective function. According to one embodiment, this weight factor is user adjustable.

According to one embodiment, the method comprises displaying respective values of the first and/or the second objective function on a display device.

Both, the displaying of the objective function and the weighting (and the adjustment thereof) of the contribution of the first objective function to the second objective function affords the user control of the computation of the adjusted plan.

The term machine setting may also refer to some attributes of a segment (that is, a particular leaf configuration in a multi-leaf collimator but other modulator devices are also envisaged herein). Attributes of segments includes any one of or a combination of the following: shape, size, MU (monitor unit), etc. Machine setting also includes the number of different such segments to be used in according to the specification (also referred to herein as the "treatment plan" or simply "plan") and in one embodiment "machine settings" refers only to said number, that is, the number of segments (from a total set of segments) to be used.

The specification also referred to herein as "treatment plan" allows controlling operation of the radiation dispenser, wherein the specification defines a dose distribution to be deposited at the object to be treated in terms of a plurality of machine settings for the radiation dispenser. The machine settings can then be used to control a modulator device (such as a multi-leaf collimator) of said dispenser to so effect a spatial intensity modulation of the treatment beam and to thereby realize a spatial intensity profile as required by dose requirements. The proposed method is envisaged in particular for DMPO (Direct Machine Parameter Optimization).

The proposed method allows addressing the situation when the user was able to create an "almost" acceptable treatment plan with respect to the balance of all global indicators and DVHs (Dose-Volume Histogram) but which suffers from local insufficiencies in the 3D dose distribution. Especially, when there are regions in the patient volume where the dose is either too high (hot spots) or too low (cold spots). Such an almost acceptable plan should be locally improved without losing its overall characteristics. In particular, the previously established trade-offs between critical structure sparing and targets conformity and the overall 3D dose distributions should be preserved. At this point the user faces a trade-off situation as to how much the plan should be allowed to change in order to correct the identified local deficiencies. The proposed DMPO-based IMRT planning allows to create a locally improved plan while retaining previously established trade-offs between critical structure sparing and target conformity Also, unlike existing schemes for DMPO-based IMRT such as above referenced Cotrutz paper, the proposed method is suitable for both, single-criteria (that is, one objective function is used) as well as multi-criteria (two or more objective functions are used) optimization. The proposed approach allows the user to directly relate the resulting local deficiencies to the machine parameters (eg, the segments). This leads to a more intuitive and easy-to-implement algorithm for clinical radiotherapy use. Moreover, the proposed method allows tight constraining of new ROIs (local deficiencies) without (or only marginally) violating other constraints during optimization.

The term "optimization" as used herein refers to a numerical algorithm that searches the solution space of machine settings to improve (minimize or maximize) the objective function. This does not necessarily imply that the final result (that is, the new treatment plan, in particular the machine settings (such as the number of segments and/or their attributes)) is "optimal" or "best" in a global sense. For one, the optimizer may converge towards a local minimum (or maximum as the case may be) rather than a global one or the optimization is aborted after a fixed number of iterations if nor changes up to a pre-defined digit of least significant after pre-defined number of iterations.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
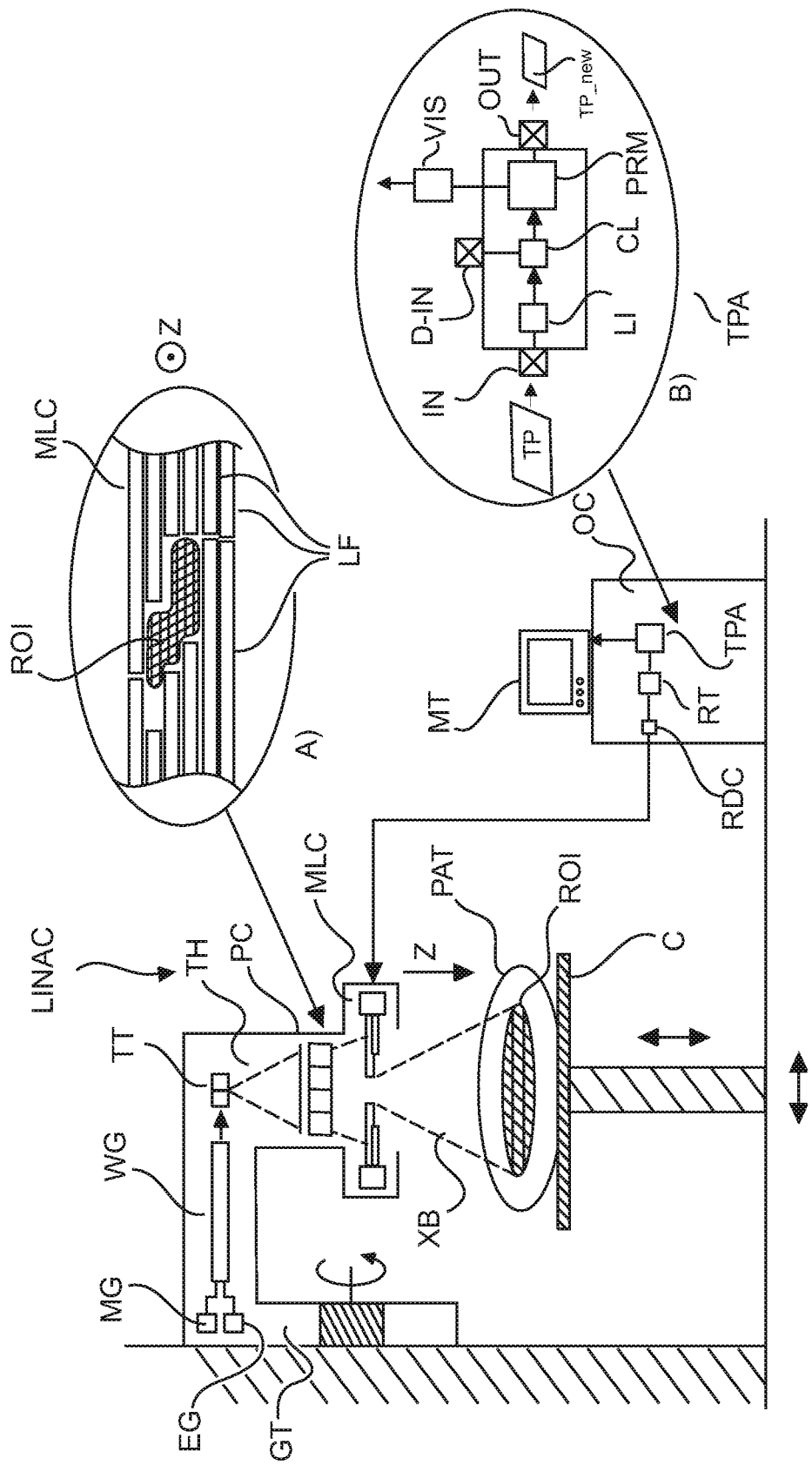
FIG. 1 shows an arrangement for radiation delivery.

With reference to FIG. 1, there is shown an arrangement for dispensing or delivering radiation in radiation therapy. The main goal in radiation therapy is to kill off cancerous tissue ROI in an animal or human patient PAT. More particularly the objective is to kill off as much of the cancerous tissue as possible but, at the same time, to spare as much of the healthy tissue as possible that surrounds the cancerous tissue.

A high energy x-ray treatment beam XB is radiated across the cancerous tissue ROI, preferably from a number of different angles.

Radiation therapy is achieved by using a linear accelerator system (referred to herein as "LINAC"). The LINAC system is to be used for IMRT. The LINAC comprises a rotatable gantry GT. The gantry is rotatable around a treatment region and around one or more axis. Only one rotation axis is shown in FIG. 1 (see the rounded arrow) but this for illustrative purposes only and in no way limiting as the LINAC may include more than one axis of rotation. In the treatment region the patient PAT to be treated is deposited on a treatment couch C.

Overall control of the LINAC's operation is from an operation console OC or work station communicatively coupled to the electronics of the LINAC system. The operation console OC may also include a control monitor MT.

The rotatable gantry includes a treatment head TH. In one embodiment, the LINAC further includes an electron gun EG, a magnetron MG and a wave guide WG. The waveguide WG is directed from the electron gun towards a tungsten target TT.

In operation, electron gun EG injects a flow of electrons into the wave guide WG. The electrons are accelerated by microwaves generated by the magnetron MG as the microwaves travel through the wave guide. The accelerated electrons impact on the tungsten target TT. This impact causes a high energetic x-ray beam to be formed. This primary x-ray beam may be collimated by a primary collimator PC arranged in the treatment head to reduce scatter. The components of the LINAC as summarized above are purely for illustrative purposes and are not limiting. In particular, other LINAC designs are likewise envisaged herein.

The so pre-collimated treatment beam then passes through a multi leaf collimator MLC arranged after the primary collimator in the treatment head TH. The multi-leaf collimated treatment beam XB then egresses the treatment head TH, travels through the treatment region and is then projected through the patent PAT and in particular through the region of interest ROI to ideally destroy all of the cancerous tissue.

One function of the multi leaf collimator MLC is to provide shaping of a cross section of the treatment beam so that the cross section at least roughly conforms to the geometric structure of the ROI. Another, more important function of the MLC for IMRT purposes is to position the leaves LF in the beam to form a plurality of openings to locally modify parts of the beam to so effect the desired radiation intensity modulation for IMRT.

Inset A) of FIG. 1 affords a view on the multi leaf collimator MLC along the projection direction Z, that is, along the propagation direction of the beam XB (in inset A), the projection direction Z extends into the paper plane). As can be seen, the multi-leaf collimator MLC is formed from a plurality of opposing pairs of highly radio-opaque, elongate structures, namely the leaves or blades LF. The opposing leaves are moveable by suitable actuators independently from each other. One or more openings can be formed anywhere within the beam's cross section between opposing pairs of leaves. Because of the leaves being independently movable and by employing a sufficient number (sometime 30 or more—although this is no way limiting) of leaf pairs with each leaf of sufficient thinness (about 5 mm), a complicated pattern of openings can be formed.

In one embodiment the MLC also includes a number of dedicated beam blocking means (sometimes referred to as "jaws") through which the overall beam shaping is effected.

For instance, the MLC may have a set of N leaves and for instance a number of jaws (for instance four but this is for illustration only and in no way limiting). The jaws are arranged in opposing pairs at north, south, west, east direction relative to the beam. For each beam direction (that is for a given treatment head position), the jaws' positions are aligned from each side as close as possible to the contour of the ROI as per said direction. This defines a reduced (for instance, but not necessarily, a square shaped) area, also called "active area", which is left open. Structures (such as the ROI) within this area can then be exposed to beam irradiation. Structures outside the active area (that is, "behind" the jaws) will not be irradiated. This reduces (or may even cancel) unwanted extra dose to the surrounding organs at risk.

A particular spatial configuration of the MLC leafs LF may be referred to herein as a "segment". The leaf positions making up the segment form an aperture (that is, one more holes or gaps left open by the MLC leafs) which may be referred to herein as the "shape" of a given segment. A "size" of a given segment is an area measure (in the order of square centimeters or square millimeters) of how large the aperture. A segment may also be described in terms of Monitor Units (MU). This is a parameter that indicates a duration of radiation delivery through this segment. In short, a segment can be defined by the following attributes: shape, size and MU.

The components of radiation dispensing arrangement 100 described thus far may be understood as the "hardware" through which radiation can be dispensed. How the MLC is to be controlled is defined by a set of control commands that processed by control commands. The control commands are then forwarded to radiation delivery controller RDC who then sends out corresponding lower level position commands to the MLC to effect the intensity modulation of the beam. The RDC controller may also be in charge to activate the beam XB and to position the treatment head TH along the required direction relative to the ROI.

More particularly, the control commands are derived from a set of machine settings that include among X-ray tube control commands that carry into effect a specific plurality of segments to be used for an IMRT of a given patient. IMRT utilizes the MLC to shape the radiation beam XB into multiple "beamlets" per beam angle, thus creating fluence maps of varying intensity. Upon delivery, these fluence-modulated beamlets sum in three dimensions to create a highly conformal dose distribution. Compared with previous radiation delivery techniques, IMRT affords more accurate radiation delivery tumor targets ROI of even irregular shape at a required or prescribed dose whilst sparing nearby normal tissues and organs at risk (OARs).

Treatment planning for IMRT is concerned with drawing up a specification ("treatment plan") of suitable segments that, when realized, allow achieving the required dose distribution across the ROI. "Inverse" treatment planning involves numerical optimization of an "objective function" (OF). Treatment goals (eg, dose requirements per location in the patient definable down to voxel level in terms of suitably detailed ROI imagery such as CT or MRI, etc) are provided by a user in numerical form as "constraints" and these are then used to optimize the objective function to eventually arrive at appropriate machine parameters (in particular the segments) to deliver an optimal treatment as per the objective function. The objective Function summarizes all clinical objectives in a numerical format. More particularly, the objective function is used to measure how much a current dose distribution differs from a desired one.

Traditionally, Fluence Map Optimization (FMO) was used to determine these segments. The FMO approach is distinct from a DMPO "Direct Machine Parameter Optimization" approach to IMRT on which the proposed arrangement is based. In FMO, the practice is to define dose constraints for tumor and normal tissues based on which an "optimal" fluence is calculated. The optimized fluence is then indirectly delivered using an ordered MLC shape-sequence computed by a "Conversion Program" also referred to as "leaf sequencing". The main limitation of FMO is that this approach does not take into account delivery constraints imposed by the MLC itself. In other words, FMO via its necessary leaf sequence post-processing may produce a leaf sequence that generally requires a large number of segments and monitor units (MUs). In contrast to the FMO approach, in DMPO-based IMRT, once the user defines the dose constraints, no "detour" via fluence maps need be taken but the underlying optimization problem is formulated in terms or machine settings (in particular the segments and the number of segments to be used) to so directly account for mechanical and delivery constraints of the particular MLC to be used. Here the machine parameters include the segment shape and weight (MU). DPMO-IMRT approach significantly reduces the number of segments and Monitor Units (MU), while able to match the quality of traditional FMO-based IMRT plans.

The objective function used in the DPMO-IMRT optimization measures optimality globally across all ROI locations. In other words although a computed treatment plan is optimal globally, there may still be local deficiencies at certain locations where the individual dose requirements are not met but these deficiencies are "balanced out" across all ROI locations when measured by the OF. Locations where such deficiencies can be observed may aptly be referred to as "cold spots" or "hot spots" (or collectively, as "deficiency spots"). In general, hotspots are volume of tissue (as per the ROI image) that would, under a given plan TP, receive doses greater than the prescribed dose as per the applicable constraints whereas cold spots are those locations that receive a dose less than the prescribed dose.

At present there is no generally accepted consensus regarding the magnitude and volume for these spots for most of tumor types. In some cases such as H&N (head & neck) for instance, it is recommended that 95% of PTV (patient volume) should be receiving the prescribed dose in which case dose spots receiving a dose >110% of the prescribed dose may be treated as hot spots. Likewise, dose spots receiving a dose <93% of the prescribed dose can be treated as cold spots. In both cases, the location is very important. However, these figures are not generally applicable for all cases and other threshold may need to be used. Also, in terms or size, hotspots whose volume exceeds 15% of the PTV volume and 2-5% of normal tissue outside PTV are critical. Similarly, cold spots whose volume exceeding 2-5% of the PTV volume may be deemed critical in H&N. It will be understood that these figures are solely exemplary and in no way limiting.

Figure 2:
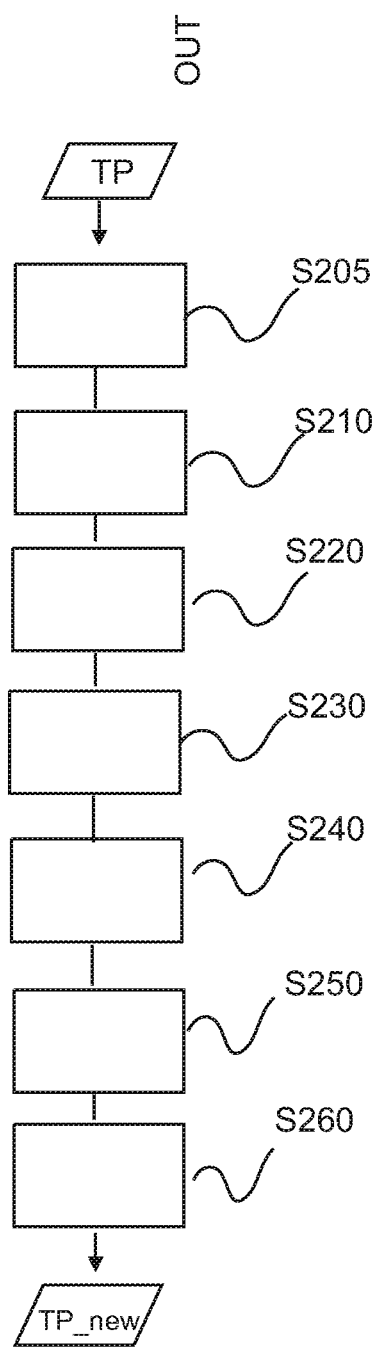
FIG. 2 shows a flow chart for adjusting a radiation treatment plan.

In order to address the occurrence of hot and/or cold spots as per an existing plan TP, the arrangement as proposed herein includes a treatment plan adjustment module TPA. The treatment plan adjustment module TPA may be run as module on the operator console or associated planning work station. Operation of treatment plan adjustment module TPA will be explained in more detail below at FIGS. 2 and 3. Broadly, the treatment plan adjustment module TPA is configured to read in an existing treatment plan TP and to process same into a new, updated treatment plan TP_new where with fewer cold and/or hot spots associated therewith or at least where the criticality of these deficiency spots are reduced.

Turning now to the treatment plan adjuster TPA in more detail, this is shown schematically in inset B) of FIG. 1. The treatment plan adjuster TPA includes a plan input port IN, a dose information input port D-IN and a plan output port OUT. The treatment plan adjuster TPA also includes a location identifier LI and a plan re-adjuster module PRM.

Broadly, and the operation of the plan adjuster is as follows:

Initially, a DMPO-based IMRT optimization is run in a first cycle with an initial set of user-specified clinical goals and delivery constraints. This, the initial plan TP, is the received at input port IN. Let us assume that this initial plan is "almost" acceptable in terms of the balance of all global objectives as measured by a first objective function F1, but the plan does suffers from local deficiencies such as at least one hot spot and/or at least one cold spot.

The location identifier LI then identifies these local dose deficiencies (ie, hot and/or cold spots). The local deficiencies in the dose distribution are delineated as new ROIs in patient model, such as an MM, CT or other volumetric imagery suitably registered with the LINAC geometry later to be used for actual dose delivery. In case of hot/cold spots these delineations can be automatic or may be based on user defined thresholds. As mentioned above, there is no generally agreed threshold information applicable for all cases for the definition of when a deficiency is considered a hold or cold spot. One set of percentage thresholds has been outlined above for the H&N case. The cold/hot spot threshold information is in generally different for each cancer case and is ultimately empirical and it is assumed herein that this cold/hot spot threshold information is available for the case at hand. The automatic identification mentioned above in relation to locations in the ROIs may also be applicable for identifying (sub-)OARs (organs at risk) not meeting the clinical goal.

After the cold/hot spot identifications, the user is then asked to specify via a suitable text or graphical user input means a dose or dose-volume limits along with penalties (importance weights) for each of these new ROIs. These new dose requirements are received by the dose information input port D-IN. To better support the user in this task, an initial set of dose or dose-volume objectives can be automatically computed by the system based on the sensitivity measure of the new ROIs with respect to the objective function. One such method has been described in Vaitheeswaran, R., Narayanan, V. S., Bhangle, J., & Nirhali, A., "TU-A-BRA-05: An Algorithm for Automated Determination of IMRT Objective Function Parameters," Medical Physics, 37(6), 3369-3369, 2010.

A new, augmented or extended objective function is then defined to form a system of objective functions: The function system includes the original, "master" objective function F1 and a new objective function F2. F1 does not include the objectives for the new ROIs as received at dose definition input port D-IN but only the old objectives/requirements from the first cycle whereas F2 does include the objectives/requirements of the new ROIs in addition to the old objectives/requirements from the first cycle. The definition of this system F1,F2 of objective functions can be done either automatically by an objective function definition tool (not shown) or may be input by the user.

The classifier module CL operates to define a segment group classification on the set of all segments to be used by the input plan. The segments that are significantly contributing to the new ROIs (hot and cold spots are identified and classified under "Critical Segment Group (CSG)". The rest of the segments are classified under "Normal Segment Group (NSG)". The segments and their attributes (weights and shapes) obtained as a result of first cycle of optimization are directly used as the starting point (initial condition) for the following second cycle of optimization.

The plan re-adjuster module then operates to perform a DMPO-based IMRT optimization in a second cycle. This second cycle of DMPO-optimization now simultaneously invoke F1 and F2 for optimization. In this second cycle of optimization, the weight and shape of "NSG segments" will be optimized using F1 as the objective function whereas the weight and shape of "CSG segments" will be optimized using F2 as the objective function.

At the end of the second cycle, the new plan TP_new is output. The user then has the option to either keep some or all of the new machine parameters as computed in the second cycle or to retain the old machine parameters based on the previous values of F1.

The initial plan TP may be computed by any plan optimizer machine or in fact may be computed by the proposed IPS, in which case the initial conditions are directly passed on two the re-adjuster PRM now using the "base" objective function F1 rather than the system of objective functions F1,F2. With reference to the flow chart in FIG. 2, the method underlying operation of treatment plan re-adjuster TPA will now be explained in more detail.

At a preliminary step S205, a first cycle of DMP-optimization is performed based on a first objective function F1. This first cycle optimization is performed with an initial set of clinical goals and delivery constraints. Here the necessary condition is to get a plan that is almost acceptable in terms of the balance of all global objectives. It is assumed that the plan suffers from local deficiencies as it causes hot and/or cold spots to emerge.

At step S210, some or all of these local defects are identified for instance via delineation as one or more ROIs.

As step S220, dose constraints for the new ROIs along with penalties are then defined.

At step S230, a dual objective function (that is, a system of two objective functions) is formed. This dual objective function includes the "master" function F1 of step S205 and an augmented or extended objective Function F2. F1 does not include the objectives of the new ROIs (local defects) and F2 does include the objectives of the new ROIs in addition to the old objectives. F2, because it includes both, the old and new objectives, is configured to negotiate a global trade-off. According to one embodiment, the dual objective function system is as per eq(1), (2) below (or mathematical equivalents thereof):

$$F1 = \Sigma_n w_n^* (D_n - P_n)^2 \quad (1)$$

$$F2 = \alpha^* F1 + \beta^* \Sigma_m w_m^* (D_m - P_m)^2 \quad (2)$$

In eqs (1), (2):

$P_n$ is the prescribed doses per each voxel n while $D_n$ is the dose computed at point n;

$w_n$ is the weight assigned to a voxel inside a particular organ or tissue;

Pm is the prescribed doses per each voxel m inside the new ROIs while $D_m$ is the dose computed at point m; and $w_m$ is the weight assigned to a voxel inside the new ROIs (local defects). As can be seen, the augmented function F2 has in one embodiment the overall stricture of a linear combination of two functional components: F1 and a functional component (the summand to the right in eq (2)) drawn to dose definition for the new ROIs.

Although the equations are drawn up with respect to voxel coordinates, this may not be so necessarily so on all embodiments. For instance, in one embodiment a coarse graining approach may be beneficial where sets of voxels are collapsed into "chunks" and the optimization is defined not on voxel level but on the level of these voxel chunks.

In equation (2), $\alpha$ and $\beta$ are the weighting factors. By setting these at a proper ratio (eg about ¼ but this is an exemplary only and the exact ratio is a matter of experience), the user can control the balance between the effect of the F1 versus F2 to maintain more or less the established trade-offs (as per F1 and $\alpha$) on the one hand, and the bias (adjustable by $\beta$) as per F2 for attempting to cure the local defects in the second cycle of optimization.

At step S240, the segment group classification is carried out. Segments as per input plan TP that are significantly contributing to the new ROIs (hot and cold spots) are classified under "Critical Segment Group (CSG)". The rest of the segments are classified under "Normal Segment Group (NSG)". Let us assume that there are N segments resulting from the first cycle of optimization. Now a "criticality analysis" is done in which those segments that significantly contribute to the new ROIs (local hot and cold spots) are identified. This can be done by measuring the percentage contribution from a given segment to the voxels inside the ROIs. A prioritization of segments based on the percentage contribution to the ROI voxels will also be performed to arrive at a "convenient" number of CSG segments.

Let N be the total number of segments resulted from first cycle of optimization, n1 be the number of segments that are classified under NSG and n2 be the number of segments that are classified under CSG such that:

$$N=n1+n2, \text{ where } n2<n1 \quad (3)$$

The following table summarizes the roles of F1,F2 versus the two groups NSG and CSG:

| Segment Group | Number of segments | Problem handled during optimization | Objective Function invoked |
|---|---|---|---|
| NSG | n1 | Overall trade-off (Global) | F1 |
| CSG | n2 | Global + Local | F2 |

Figure 3:
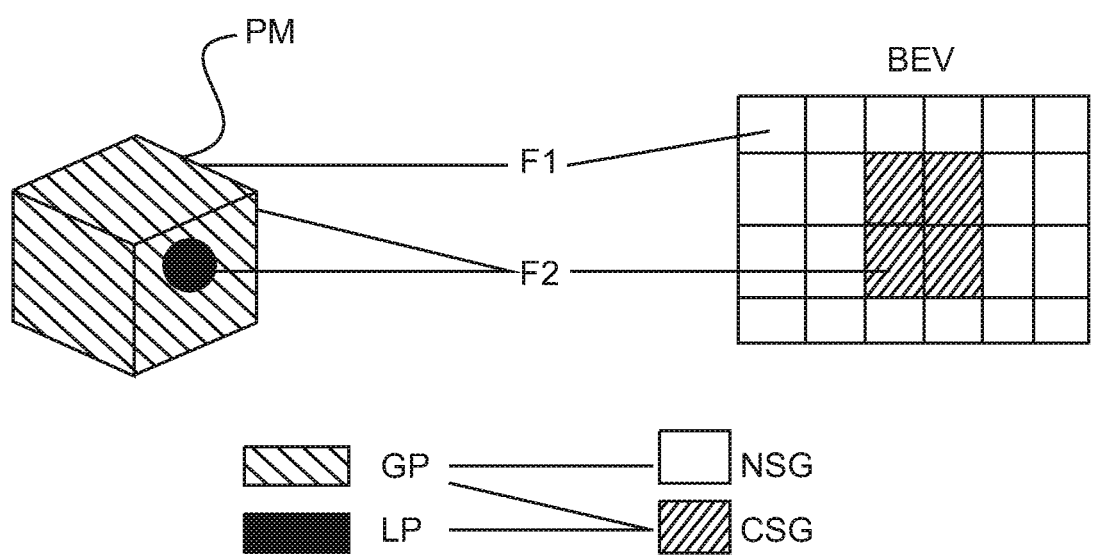
FIG. 3 is graphical representation of an aspect of the method as per FIG. 2.

FIG. 3 is an illustration of segment grouping and allocation of objective functions for the segment groups. The locations of hot and or cold spots (one is shown as a black dot) are as per a suitable patient model PM, eg a CT image or other suitable volumetric imagery. Locations that receive the correct dose are shown as hatched in PM. The involved segments are shown as a Beamlet eye view (BEV) image. F1 looks after the global (optimization) problem (GP) whereas extended objective function F2 looks after the global (GP) and local (LP) optimization problem. Segments in CSG are shown hatched as per BEV and segments as per NSG are shown clear. The association between a location in PM and the contributing segments can be established by running ray-tracing algorithms. Such ray-tracing algorithms have been described for instance M de Greef et al, "Accelerated ray tracing for radiotherapy dose calculations on a GPU", Medical Physics 36, 4095 (2009) or C Fox et al "Fast voxel and polygon ray-tracing algorithms in intensity modulated radiation therapy treatment planning", Medical Physics 33, 1364 (2006).

At step S250, a second cycle of optimization is performed based on objective function system as per eq (1) and (2).

The segments and their attributes (size, shape and weight) resulted from the first cycle of optimization are directly used as the starting point (initial condition) for the second cycle of optimization. The second cycle is initiated, which will simultaneously use F1 and F2 for optimization. In this cycle of optimization, the size, shape and weight of "NSG segments" will be optimized using F1; the size, shape and weight of "CSG segments" will be optimized using F2.

This second optimization run allows all (N) the segments to "look after" the global trade-off problem, while a smaller number of segments (n2) to "look after" the local defects in addition to the global trade-off problem. In this way, one can preserve, during the second cycle of optimization, some, most or even all of the initial conditions obtained from the first cycle of optimization.

Moreover, running the optimization based on the dual objective function (1), (2) (which may also be considered as an objective function partitioning optimized over the space of segments likewise partitioned into NSG and CSG) allows the user to control the amount (measurable as a ratio or percentage) by which a given NSG segment is allowed to change in terms of segment size, shape and weight during the second cycle with respect to its attributes as per the first cycle of optimization. Eventually, the second cycle of optimization has been observed to lead in most (if not all) circumstances to a locally improved plan that also retains the previously established trade-offs between sparing of critical structure on the one hand and target conformity on the other hand.

As per eq (3), since only a relatively small (having n2 elements) subset of "highly influential" CGS segments are assigned to "cure" the local defects, one can specify a tight constraint in respect of the new ROIs and still avoid disturbing the previously established trade-offs in the first cycle of optimization. A ratio of n2/n1 in the order of about ¼ has been observed to lead to an improvement of the plan but other ratios my also work in other circumstances and are envisaged herein.

Moreover, the weighting factors $\alpha$ and $\beta$ included in the objective function F2 will allow the user to control the balance between maintaining the established trade-offs (from the previous first cycle) and curing the local defects in the second cycle of optimization. This gives one more level of convenience to the user in handling the local defects and to configure and tailor the plan adjuster to the particulars of the task at hand. The weighting factors for the two objective functions F1,F2 are user adjustable and the system includes in one embodiment a text or graphic based input of $\alpha$ and/or $\beta$ at the start of the second cycle optimization or during execution of the second cycle optimization.

At the conclusion of the second cycle of optimization, user can verify if the already established global trade-offs have been compromised or not by looking at the current value of F1. The user is then at liberty to keep the current machine parameters or retrieve the initial machine parameters based on the current values of F1, F2 and other plan quality indicators.

The system may further comprise a visualizer tool VIS to display in step S260 the respective values of F1 and/or F2 on a viewport or two dedicated viewports on screen MT during execution of the second cycle optimization. This allows the user to better follow the course of the optimization.

In one embodiment, the visualizer tool VIS may be configured to display at step the segments under their respective group (NSG and CSG) or may be configured to display a "segment map" where the association between a segment and its group is visualized.

In one embodiment, the change of segment attributes in the two NSG segments and CSG segments is displayed in respective, dedicated user interfaces simultaneously during the optimization run.

In one embodiment, the visualizer tool VIS may be configured to visualize the in a viewport the criticality of a given segment with respect to a local defect (hot or cold spots) is detectable. The criticality may be measured as mentioned above in percentage terms that indicted the amount by which said segment contributes controlling radiation deposition at said cold or hot spot. Any combination (some or all) of the above described display embodiments as per visualizer tool VIS is envisaged herein at display step S260.

In sum, the proposed approach is configured to maintain the overall trade-offs between critical structure sparing and target conformity (global problem), while able to remove local dose defects. Once the local defects are identified after first cycle of optimization, the whole problem is split into two parts as mentioned earlier. Similarly, two segment groups are identified. The novelty of our approach is that these two different segment groups are made to invoke two different objective functions (F1 and F2) during second cycle of optimization. In this process, more number of segments are assigned to look at the overall trade offs (excluding the local defects), while a small number n2 of "highly influential" segments are assigned to look after the local defects in addition to the overall trade off problem. In other words, few segments get additional assignments during the second cycle. It is then proposed herein to preserve most of initial conditions obtained from the first cycle during the second cycle of optimization. Basically, the number of segments required to solve the local problem is pre-determined in this approach. In this way it is ensured that the second cycle does not cause a huge disturbance to the existing plan quality, while able to rectify the local defects. Although some NSG segments will also undergo a change (that is, have one or more of their attributes changed) during second cycle of optimization. However, because of the partitioning of objective function, the magnitude of change in the attributes of NSG segments is expected to be minimal. Also, it is to be noted that the second cycle is a complete optimization that optimizes segment size, shape and weight.

The proposed method affords the following advantages:

A new way is provided to balance between established trade-offs and local dose defects, "trade-off" being the balance achieved in the first optimization between target coverage and normal tissue sparing.

The weighting factors $\alpha$ and $\beta$ included in the objective function extended objective function allows the user to actively determine the way the local defects are to be handled.

The method allows tightly constraining of new ROIs without violating other constraints during optimization.

Another unique advantage is that the method affords some degree of voxel-specificity of the optimization process without going for a full voxel-based optimization The method can be used with benefit in an auto-plan environment and can enhance the efficiency of said auto-plan environment.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an"

The invention claimed is:

1. A method of adjusting a first specification of a dose distribution in an object to be exposed to radiation by a linear accelerator, the first specification being computed based on an objective function, the objective function defining a dose requirement for at least one respective location in an object in terms of a machine setting for the linear accelerator, the method comprising the steps of:
   based on the first specification, identifying at least one location for which a respective dose requirement per the objective function is not met relative to a threshold;
   receiving a new dose requirement for the identified at least one location; and
   computing a second specification based on two objective functions including the objective function and an extended objective function, formed from the objective function, wherein the extended objective function includes at least one of the dose requirements as per the objective function in addition to the new dose requirement.

2. The method of claim 1, further comprising:
   classifying the machine settings into a critical group and a normal group, wherein a machine setting associated with the at least one identified location is classified into the critical group, whereas a machine setting associated with the at least one identified location or a different location is classified into the normal group when the respective dose requirement as per the objective function is met.

3. The method of claim 2, wherein there is at least one more machine setting in the normal group than there is in the critical group.

4. The method of claim 2, wherein the objective function is restricted to the normal group of machine settings and wherein the extended objective function is restricted to the critical group of machine settings.

5. The method of claim 1, wherein the extended objective function includes at least one user adjustable weight factor to weight a contribution of the objective function to the extended objective function.

6. The method of claim 1, further comprising displaying respective values of the objective function or of the extended objective function, or both, on a display device (MT).

7. An apparatus for adjusting a first specification of a dose distribution in an object to be exposed to radiation by a radiation dispenser, the specification being computed based on an objective function, the objective function defining a dose requirement for at least one respective location in an object in terms of a machine setting for said radiation dispenser, the apparatus comprising:
   an input port configured to receive the first specification;
   a location identifier module configured to identify, based on the first specification, at least one location for which a respective dose requirement as per the objective function is not met relative to a threshold;
   a dose input port configured to receive a new dose requirement for the identified at least one location; and
   a plan re-adjuster module configured to compute a second specification based on two objective functions including the objective function and an extended objective function, formed from the objective function, wherein the extended objective functions includes at least one of the dose requirements as per the objective function in addition to the new dose requirement.

8. The apparatus of claim 7, comprising:
   a classifier configured to classify the machine settings into a critical group and a normal group, wherein a machine setting associated with the at least one identified location is classified into the critical group, whereas a machine setting associated with a different location is classified into the normal group when the respective dose requirement as per the objective function is met.

9. The apparatus of claim 7, comprising a visualizer configured to effect display of respective values of the extended objective function or the extended objective function, or both, on a display device.

10. The method of claim 1, wherein the extended objective function comprises objectives of new regions of interest.

11. The apparatus of claim 7, wherein the extended objective function comprises objectives of new regions of interest.

12. A system for adjusting a first specification of a dose distribution in an object to be exposed to radiation by a radiation dispenser, the first specification being computed based on an objective function, the objective function defining a dose requirement for at least one respective location in an object in terms of a machine setting for said radiation dispenser, comprising:
   a tangible non-transitory storage medium that stores instructions, and
   a processor that executes the instructions,
   wherein, when executed by the processor, the instructions cause the processor to implement a method, comprising:
   based on the first specification, identifying at least one location for which a respective dose requirement per the objective function is not met relative to a threshold;
   receiving a new dose requirement for the identified at least one location; and
   computing a second specification based on two objective functions including the objective function and an extended objective function, formed from the objective function, wherein the extended objective function includes at least one of the dose requirements as per the objective function in addition to the new dose requirement.

13. The system of claim 12, wherein the method further comprises:
   classifying the machine settings into a critical group and a normal group, wherein a machine setting associated with the at least one identified location is classified into the critical group, whereas a machine setting associated with the at least one identified location or a different location is classified into the normal group when the respective dose requirement as per the objective function is met.

14. The system of claim 13, wherein there is at least one more machine setting in the normal group than there is in the critical group.

15. The system of claim 13, wherein the objective function is restricted to the normal group of machine settings and wherein the extended objective function is restricted to the critical group of machine settings.

16. The system of claim 12, wherein the extended objective function includes at least one user adjustable weight factor to weight a contribution of the objective function to the extended objective function.

17. The system of claim 12, wherein the method further comprises displaying respective values of the objective function or the extended objective function, or both, on a display device.

* * * * *